United States Patent [19]

Eventoff et al.

[11] Patent Number: 4,841,978
[45] Date of Patent: Jun. 27, 1989

[54] ULTRASONIC SCANNING DEVICE WITH ELASTIC PUMPER

[75] Inventors: Arnold T. Eventoff, Rye Brook; Wyatt S. Newman, New York, both of N.Y.

[73] Assignee: North American Philips Corporation, New York, N.Y.

[21] Appl. No.: 685,371

[22] Filed: Dec. 24, 1984

[51] Int. Cl.[4] .............................................. A61B 10/00
[52] U.S. Cl. .................... 128/660.09; 73/620
[58] Field of Search ................. 128/660–661; 73/618–620

[56] References Cited

U.S. PATENT DOCUMENTS

| | | | |
|---|---|---|---|
| 4,399,703 | 8/1983 | Matzuk | 128/660 X |
| 4,433,691 | 2/1984 | Bickman | 128/660 |
| 4,479,388 | 10/1984 | Matzuk | 128/660 X |
| 4,515,017 | 5/1985 | McConaghy | 128/660 X |

Primary Examiner—Francis Jaworski
Attorney, Agent, or Firm—Jack E. Haken

[57] ABSTRACT

An ultrasonic scanning device includes a stator and a rotor pivotably mounted on the stator for oscillation around the axis of rotation. The rotor (or stator) has two elastic bumper stops spaced from the axis of rotation and spaced from each other. An elastic bumper is attached to the stator (or rotor) and arranged between the bumper stops. The resulting scanning device conserves energy by converting kinetic energy in one direction to potential energy, and then by converting the potential energy back into kinetic energy in the opposite direction.

20 Claims, 5 Drawing Sheets

FIG.6
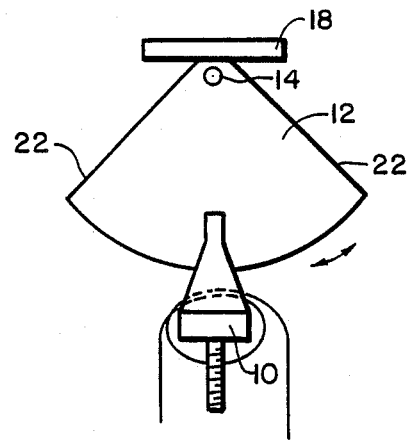
FIG.7
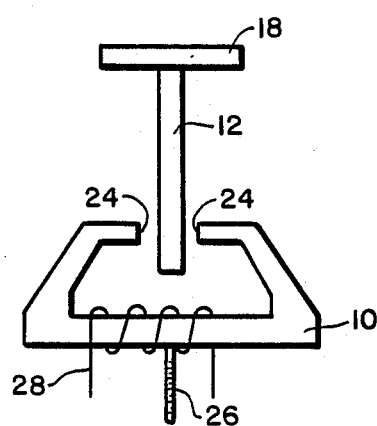
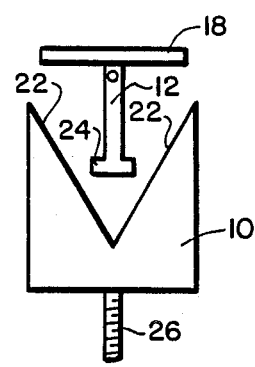
FIG.8

ULTRASONIC SCANNING DEVICE WITH ELASTIC PUMPER

BACKGROUND OF THE INVENTION

The invention relates to scanning devices. More particularly, the invention relates to devices for scanning an ultrasonic transducer across a body, in order to produce an image of a cross-section through the body. Such devices are used, for example, in medical diagnostics.

In ultrasonic "A-scanners", an ultrasonic transducer generates an acoustic pressure signal and projects the signal in a straight line through a body. The projected signal is scattered along its path of propagation, and as a result generates an echo acoustic pressure signal. The echo pressure signal contains information regarding the nature of the body along the path of propagation. The ultrasonic transducer receives the echo pressure signal, and converts it into an electric signal.

A two-dimensional image of a cross-section through the body is obtained in an ultrasonic "A-scanner", by pivoting the ultrasonic transducer through a selected angular range in order to scan the cross-sectional layer. Each electrical echo signal represents an image of a radial line in the layer; all the electrical echo signals together represent an image of a pie-shaped cross-sectional layer of the body. By suitable processing of the electrical echo signals, an image of the layer can be displayed on, for example, a cathode ray tube screen.

In practice, the ultrasonic transducer is not pivoted only one time through the selected angular range. In practice, the transducer is oscillated back and forth many times. Each repeated oscillation of the transducer produces a new image of the cross-sectional layer of the body, thus resulting in real-time imaging of the layer.

The motor used to oscillate the ultrasonic transducer must supply torque (i) to periodically reverse the direction of rotation of the transducer, (ii) to overcome frictional losses, for example due to the viscous drag of the liquid in which the transducer is typically immersed, and (iii) to cause the transducer to track a reference signal when a servo-control system is utilized. The torque required to overcome frictional losses is usually relatively small. Moreover, preferably the angular velocity of the transducer is constant throughout the scan, thereby requiring no tracking torque. Accordingly, typically 75%–90% of the torque requirement of the scanning device arises from the direction-reversal requirement.

The direction-reversal torque requirement can be explained with reference to FIG. 1, in which the angular displacement of an oscillating transducer as a function of time is shown. At each reversal of direction, the transducer is accelerated for a time, $\Delta t$, in order to reverse its direction.

SUMMARY OF THE INVENTION

It is an object of the invention to provide an oscillating scanning device whose scan direction can be reversed by the application of a relatively low torque.

It is another object of the invention to provide an oscillating scanning device whose scan direction can be reversed in a short time, $\Delta t$.

According to the invention, a scanning device, particularly an ultrasonic scanning device, comprises a stator, a rotor, an ultrasonic transducer, and means for causing the rotor to oscillate around the axis of rotation. The ultrasonic transducer is mounted on the rotor.

The rotor has two elastic bumper stops arranged spaced from the axis of rotation and spaced from each other. The scanning device further comprises an elastic bumper attached to the stator and arranged between the bumper stops of the rotor. What is meant by "elastic" bumpers and bumper stops is any bumpers or bumper stops through which the stator and rotor can collide, and which will return a significant portion of the kinetic energy of the rotor before the collision to the rotor after the collision.

The invention advantageously reduces the torque requirement for reversing the direction of the rotor by converting the kinetic energy of the rotor in one direction to potential energy, and then converting the potential energy back to kinetic energy in the opposite direction. First, the kinetic energy of the rotor in one direction is converted to potential energy in the elastic bumper during the period $\approx \Delta t/2$, until the angular velocity of the rotor is zero. Most of the kinetic energy is converted into potential energy. Next, the potential energy stored in the elastic bumper is returned to kinetic energy in the rotor by accelerating the rotor in the opposite direction during an additional period of time $\approx \Delta t/2$. Most of the stored potential energy is converted into kinetic energy. By increasing the stiffness of the elastic bumper and of the bumper stops, the reversal time, $\Delta t$, can be reduced as desired.

According to one aspect of the invention, each bumper stop may be a planar surface. The bumper stop surfaces may also intersect each other along a line located between the axis of rotation and the elastic bumper.

In order to adjust the peak amplitude of oscillation of the rotor, the elastic bumper is preferably displaceable toward or away from the rotor. Preferably, the elastic bumper is displaceable along a radius from the axis of rotation.

The bumper and bumper stops preferably are made of steel having minimum internal damping to minimize energy losses. Other materials which could be used include, but are not limited to, beryllium-copper, phosphor-bronze, or even some ceramic or glass-like materials. If some additional damping can be tolerated, natural or synthetic rubbers can be used.

Alternatively, the elastic bumper may be a stiff cantilever spring, for example a leaf spring.

In another alternative form of the invention, the bumper and bumper stops are magnetized such that the bumper stops exert repulsive forces on the bumper.

Still another form of the invention uses a magnetically permeable stator and rotor forming a magnetic circuit. Means are provided for generating magnetic flux in the magnetic circuit, such that the direction of the rotor is reversed whenever the edge of the rotor swings up to the stator pole faces.

Where accurate control of the, rotor is desired, the invention may include means for generating a reference signal representing the desired angular position or the desired velocity of the rotor, and means for generating either a position signal or a velocity signal representing the actual position or velocity of the rotor. Means responsive to the difference between the reference signal and either the position or velocity signal cause the rotor to oscillate around the axis of rotation in the desired manner.

Preferably, when the reference signal represents the desired velocity of the rotor, the means for generating the reference signal includes means for changing the sign of the reference signal each time the elastic bumper contacts a bumper stop.

Where the reference signal represents the desired angular position of the rotor, the absolute value of the slope of the reference signal is constant. The means for generating the reference signal then includes means for changing the sign of the slope of the reference signal each time the elastic bumper contacts a bumper stop.

BRIEF DESCRIPTION OF THE DRAWING

FIG. 6 is a front elevational view of part of an ultrasonic scanning device having magnetic bumpers according to an embodiment of the invention.

FIG. 7 is a side elevational view of the device of FIG. 6.

FIG. 8 is a front elevational view of part of another embodiment of an ultrasonic scanning device according to the invention.

DESCRIPTION OF THE PREFERRED EMBODIMENTS

Figure 1:
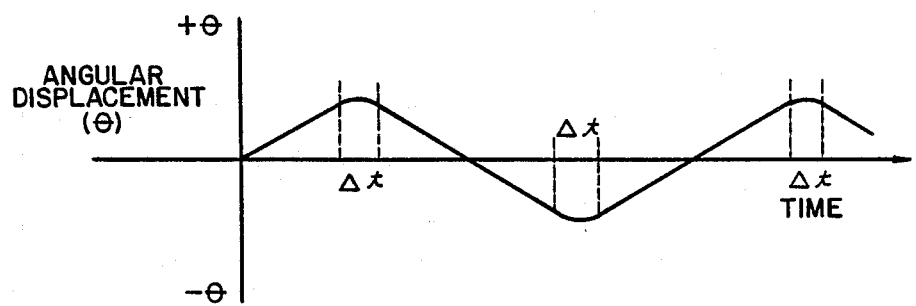
FIG. 1 is a plot illustrating a typical angular displacement versus time curve for a rotor in an ultrasonic scanning device.
Figure 2:
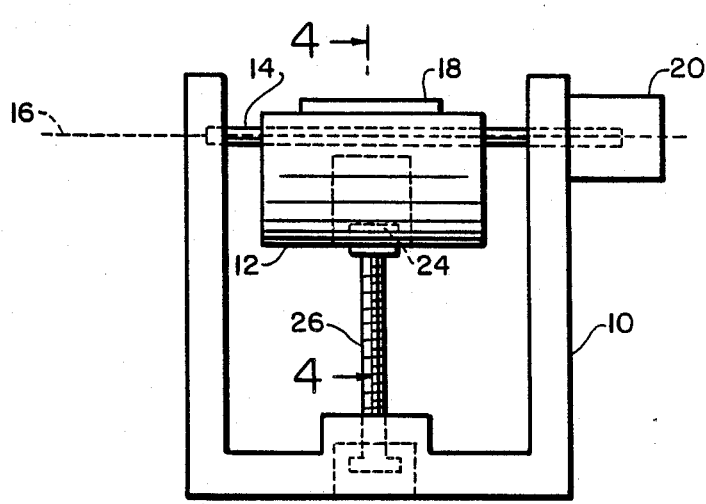
FIG. 2 is a front elevational view, partly schematic, of an embodiment of an ultrasonic scanning device according to the invention.
Figure 3:
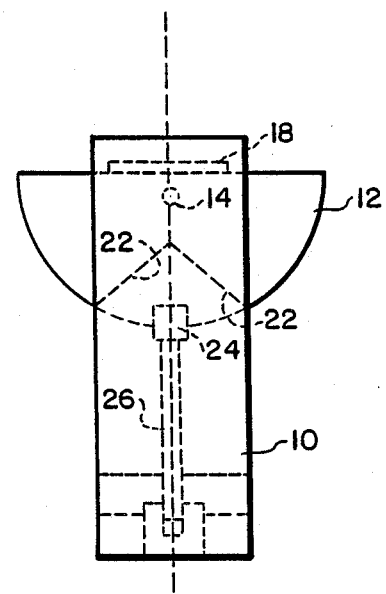
FIG. 3 is a side elevational view of the ultrasonic scanning device of FIG. 2.
Figure 4:
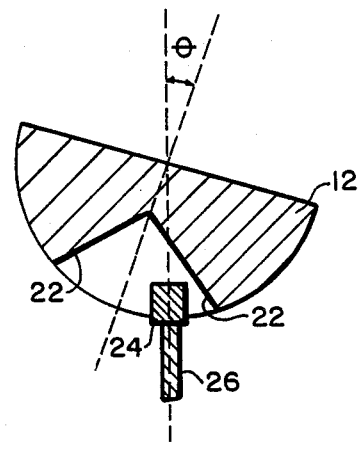
FIG. 4 is a cross-sectional view along the line IV—IV of FIG. 2, of a part of the ultrasonic scanning device of FIG. 2.

FIGS. 2, 3 and 4 show an embodiment of an ultrasonic scanning device according to the present invention. The device includes a stator 10 and a rotor 12. The rotor 12 is arranged on a shaft 14 to pivot around an axis of rotation 16. One end of the shaft 14 is mounted in the stator in a recess in the stator 10. The other end of shaft 14 arranged in a bore in the stator 10. Alternatively, the rotor 12 can be pivotably mounted on the stator 10 by way of ball bearings or other bearings.

When the scanning device according to the invention is part of ultrasonic medical equipment, the rotor 12 bears an ultrasonic transducer 18 on the upper surface thereof. As the rotor 12 oscillates about the axis of rotation 16, the ultrasonic transducer 18 also rotates with the rotor.

The rotor 12 and ultrasonic transducer 18 are caused to oscillate around the axis of rotation 16 by a motor 20 (schematically shown in FIG. 2). The motor 20 may be any known motor capable or reversing its direction of rotation periodically. For example, see U.S. Pat. No. 4,092,867.

As shown in FIGS. 2 through 4, the rotor 12 in the illustrated embodiment of the present invention has a triangular-shaped slot cut out of the bottom thereof. The slot has two elastic bumper stops 22 which are side surfaces of the slot. Bumper stops 22 are spaced from the axis of rotation 16 and are spaced from each other.

The scanning device also includes an elastic bumper 24. Bumper 24 is arranged between the bumper stops 22. Bumper 24 is attached to the stator 10 by way of a threaded shaft 26. As shown in FIG. 2, threaded shaft 26 passes through a threaded slot in the base of the stator 10. By turning the threaded shaft 26 (either manually or by an electric motor), the elastic bumper 24 can be displaced toward or away from the rotor 12 in a precisely controlled manner.

As is apparent from FIGS. 3 and 4, the maximum angular displacement of the rotor 12 about the axis of rotation 16 can be controlled by raising or lowering the elastic bumper 24 via the threaded screw 26. For this purpose, each bumper stop 22 may be a planar surface. The bumper stop surfaces shown in FIGS. 3 and 4 intersect each other along a line located between the axis of rotation 16 and the elastic bumper 24. While such a geometry is preferred, other geometries can also be designed to achieve similar results.

It is also preferred that when a displaceable bumper 24 is used, the bumper be displaceable along a radius from the axis of rotation 16. Again, while this geometry is preferred, other geometries can be used to produce similar results.

While bumper 24 in the illustrated embodiment of the invention is displaceable, if the amplitude of oscillation is to be fixed, the bumper 24 need not be displaceable at all.

In the operation of the scanning device of FIGS. 2 through 4, the direction of rotation of rotor 12 is reversed each time a bumper stop 22 physically contacts the elastic bumper 24. Alternatively, the bumper stops 22 and bumper 24 cam be magnetized such that the bumper stops 22 exert repulsive forces on the bumper 24. If the magnetic repulsive forces are strong enough relative to the angular momentum of the rotor 12, the direction of rotation of the rotor 12 can be reversed before the elastic bumper stops 22 physically contact the elastic bumper 24.

A particularly advantageous magnetic bumper arrangement is shown in FIGS. 6 and 7. In this arrangement, the stator 10 and rotor 12 are highly magnetically permeable and form a magnetic circuit (as shown in FIG. 7). As the rotor 12 oscillates between the end faces (bumper 24) of the pole piece (stator 10) there is no change in the magnetic reluctance of the circuit. Therefore, the magnetic circuit generates no forces affecting the oscillation of rotor 12.

However, whenever rotor 12 attempts to rotate so far that either of its edges 22 (bumper stops) pass between the end faces 24 of the stator 10, the reluctance of the magnetic circuit suddenly increases greatly. As a result, the magnetic circuit generates strong forces opposing the motion of the rotor 12. These forces will reverse the direction of rotation of the rotor 12.

Magnetic flux may be generated in the magnetic circuit by passing an electric current through coil 28, or by inserting a permanent magnet in the magnetic circuit.

In an ultrasonic scanning device according to the invention, the angular velocity of the transducer should be constant throughout the scan, changing direction each time the peak angular displacement is reached. To achieve this requirement, a servo-control system can be used.

Figure 5:
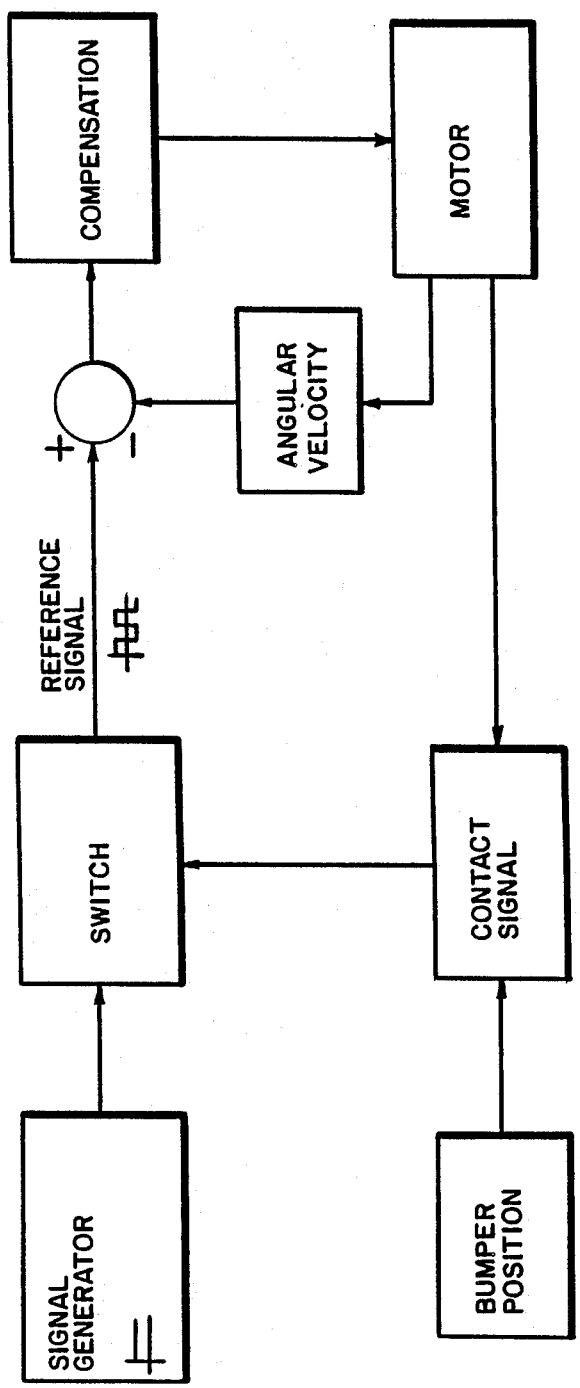
FIGS. 5A and 5B are block diagrams of servo systems for controlling the oscillatory motion of the rotor in an ultrasonic scanning device according to the invention.

FIG. 5A shows a simple embodiment of a servo-control system in which velocity feedback is used. A reference signal is generated representing the desired angular velocity of the rotor 12 around the axis of rotation 16. From this is subtracted a signal representing the actual angular velocity of the rotor 12, to produce a difference signal. The difference signal is compensated, for stability, to produce a drive signal for driving the motor 20.

The reference signal is a square wave signal symmetrical about the time axis. Each time an elastic bumper stop 22 contacts the elastic bumper 24, a contact signal activates a switch. The switch changes the sign of a constant voltage signal (step function) generated by a signal generator, in order to produce the reference signal.

A signal indicating contact between the bumper stops 22 and elastic bumper 24 may be generated by making the bumper 24 and rotor 12 out of electrically conductive materials, and by applying an electric potential therebetween. An electric current pulse will then be generated each time contact is made.

A so-called "contact signal" can be generated in the case of magnetic bumpers by using a Hall effect proximity sensor, or by sensing the change in reluctance of the magnetic circuit. Whichever sensor is used should be adjusted to emit the "contact signal" before the rotor reaches its desired peak amplitude, for example when the rotor reached 90% of its peak amplitude.

The angular velocity signal can be generated by using any conventional position sensor, and by differentiating the sensor output.

Figure 5B:
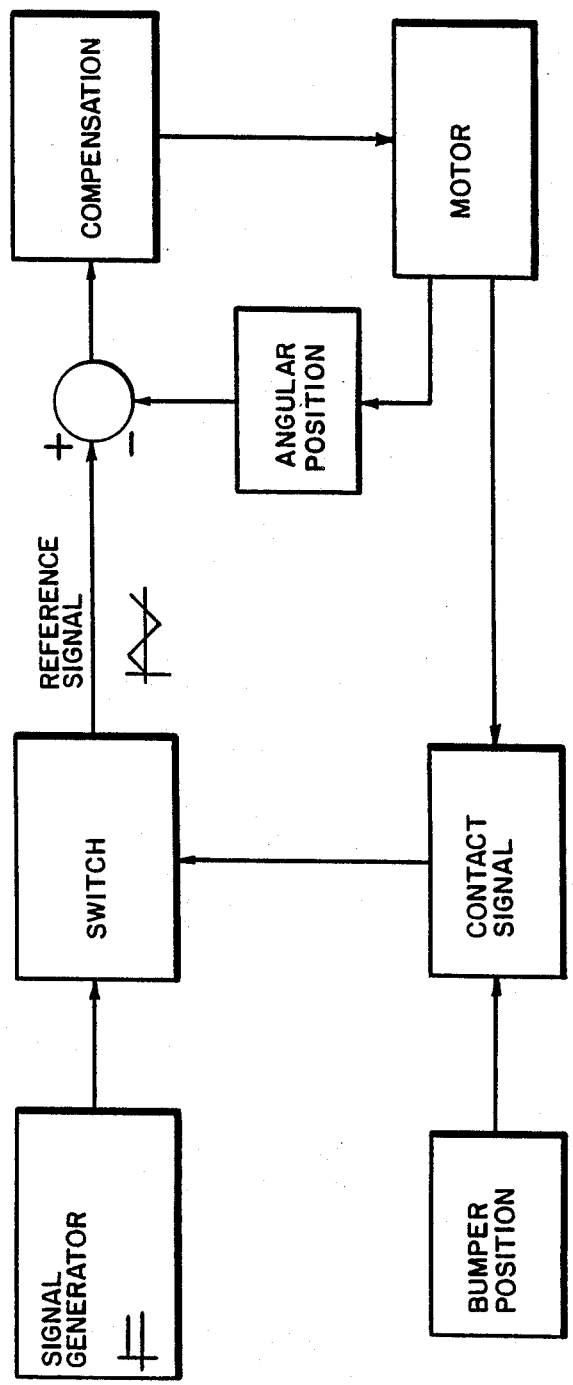

Alternatively, the servo-control system can be based upon position feedback. In this case, shown in FIG. 5B, the reference signal will be a triangular wave, symmetrical about the time axis. Each time an elastic bumper stop 22 contacts an elastic bumper 24, a switch is activated. The switch changes the sign of the slope (rate of change as a function of time) of a ramp function generated by a signal generator to produce the reference signal.

While the invention has been shown with the bumper stops provided on the rotor and the bumper provided on the stator, one with ordinary skill in the art would recognize that these elements could be interchanged. The bumper stops could be provided on the stator, and the bumper could be provided on the rotor, as shown, for example, in FIG. 8.

What is claimed:

1. An ultrasonic scanning device comprising:
   a stator;
   a rotor having an axis of rotation, said rotor being pivotably mounted on the stator for oscillation around the axis of rotation;
   an ultrasonic transducer mounted on the rotor; and
   means for causing the rotor to oscillate around the axis of rotation;
   characterized in that:
   the rotor has two elastic bumper stops arranged spaced from the axis of rotation and spaced from each other;
   the device further comprises an elastic bumper attached to the stator and arranged between the bumper stops; and
   the means for oscillating the rotor oscillates the rotor with substantially constant angular velocity, and reverses the direction of the rotor by elastic collisions between the bumper stops.

2. An ultrasonic scanning device as claimed in claim 1, characterized in that each bumper stop is a planar surface.

3. An ultrasonic scanning device as claimed in claim 2, characterized in that the elastic bumper is displaceable toward or away from the rotor.

4. An ultrasonic scanning device as claimed in claim 3, characterized in that the elastic bumper is displaceable along a radius from the axis of rotation.

5. An ultrasonic scanning device as claimed in claim 4, characterized in that the bumper stop surfaces intersect each other along a line located between the axis of rotation and the elastic bumper.

6. An ultrasonic scanning device as claimed in claim 4, characterized in that the bumper and bumper stops are made of metal.

7. An ultrasonic scanning device as claimed in claim 6, characterized in that the bumper and bumper stops are made of steel.

8. An ultrasonic scanning device as claimed in claim 4, characterized in that the bumper and bumper stops are magnetized such that the bumper stops exert repulsive forces on the bumper.

9. An ultrasonic scanning device as claimed in claim 1, characterized in that:
   the stator comprises a magnetically permeable pole piece having end faces;
   the rotor comprises a magnetically permeable member arranged to pass between the end faces of the stator as the rotor oscillates, said stator and rotor forming a magnetic circuit; and
   the device further comprises means for generating magnetic flux in the magnetic circuit.

10. An ultrasonic scanning device as claimed in claim 1, characterized in that the elastic bumper is displaceable toward or away from the rotor.

11. An ultrasonic scanning device as claimed in claim 10, characterized in that the device further comprises:
    means for generating a reference signal representing the desired angular velocity of the rotor around the axis of rotation;
    means for generating a velocity signal representing the actual angular velocity of the rotor around the axis of rotation; and
    means responsive to the difference between the reference signal and the velocity signal for driving the means for causing the rotor to oscillate around the axis of rotation.

12. An ultrasonic scanning device as claimed in claim 11, characterized in that the reference signal generating means comprises:
    means for generating a signal indicating contact between the elastic bumper and a bumper stop;
    means for generating a step function electrical signal; and
    means for changing the sign of the electrical signal in response to the contact signal.

13. An ultrasonic scanning device as claimed in claim 10, characterized in that the device further comprises:
    means for generating a reference signal representing the desired angular position of the rotor around the axis of rotation;
    means for generating a position signal representing the actual angular position of the rotor around the axis of rotation; and
    means responsive to the difference between the reference signal and the position signal for driving the means for causing the rotor to oscillate around the axis of rotation.

14. An ultrasonic scanning device as claimed in claim 13, characterized in that the reference signal generating means comprising:

means for generating a contact signal indicating contact between the elastic bumper and a bumper stop;

means for generating an electrical signal with a constant rate of change as a function of time; and means for changing the sign of the rate of change of the reference signal as a function of time in response to the contact signal.

15. A scanning device comprising:

a stator;

a rotor having an axis of rotation, said rotor being pivotably mounted on the stator for oscillation around the axis of rotation; and means for causing the rotor to oscillate around the axis of rotation;

characterized in that:

the rotor has two elastic bumper stops arranged spaced from the axis of rotation and spaced from each other;

the device further comprises an elastic bumper attached to the stator and arranged between the bumper stops; and the means for oscillating the rotor oscillates the rotor with substantially constant velocity, and reverses the direction of the rotor by elastic collisions between the bumper and the bumper stops.

16. A scanning device as claimed in claim 15, characterized in that the elastic bumper is displaceable toward or away from the rotor.

17. An ultrasonic scanning device comprising:

a stator;

a rotor having an axis of rotation, said rotor being pivotably mounted on the stator for oscillation around the axis of rotation;

an ultrasonic transducer mounted on the rotor; and means for causing the rotor to oscillate around the axis of rotation;

characterized in that:

the stator has two elastic bumper stops arranged spaced from the axis of rotation and spaced from each other;

the device further comprises an elastic bumper attached to the rotor and arranged between the bumper stops; and the means for oscillating the rotor oscillates the rotor with substantially constant velocity, and reverses the direction of the rotor by elastic collisions between the bumper and the bumper stops.

18. An ultrasonic scanning device as claimed in claim 17, characterized in that the bumper stops are displaceable toward or away from the rotor.

19. An ultrasonic scanning device as claimed in claim 17, characterized in that the device further comprises:

means for generating a reference signal representing the desired angular velocity of the rotor around the axis of rotation;

means for generating a velocity signal representing the actual angular velocity of the rotor around the axis of rotation; and means responsive to the difference between the reference signal and the velocity signal for driving the means for causing the rotor to oscillate around the axis of rotation.

20. An ultrasonic scanning device as claimed in claim 17, characterized in that:

the rotor comprises a magnetically permeable pole piece having end faces;

the stator comprises a magnetically permeable member arranged between the end faces of the rotor, said stator and rotor forming a magnetic circuit; and the device further comprises means for generating magnetic flux in the magnetic circuit.

* * * * *